United States Patent [19]

Pasricha et al.

[11] Patent Number: 5,846,235

[45] Date of Patent: Dec. 8, 1998

[54] ENDOSCOPIC CRYOSPRAY DEVICE

[75] Inventors: Pankaj Jay Pasricha, Galveston, Tex.;
Anthony N. Kalloo, Columbia, Md.;
John G. Baust; Lawrence Potorff,
both of Rockville, Md.

[73] Assignees: Johns Hopkins University, Baltimore;
Cryomedical Sciences, Inc., Rockville,
both of Md.

[21] Appl. No.: 840,290

[22] Filed: Apr. 14, 1997

[51] Int. Cl.$^6$ ............................................ A61B 17/36
[52] U.S. Cl. ............................ 606/23; 606/20; 606/21
[58] Field of Search ........................ 606/20, 21, 22, 606/23, 24, 25, 26, 140

[56] References Cited

U.S. PATENT DOCUMENTS

| | | |
|---|---|---|
| 3,125,096 | 3/1964 | Antiles et al. . |
| 3,425,419 | 2/1969 | Dato . |
| 3,651,813 | 3/1972 | Bryne . |
| 3,823,718 | 7/1974 | Tromovitch . |
| 3,859,986 | 1/1975 | Okada et al. . |
| 3,886,945 | 6/1975 | Stumpf et al. . |
| 3,924,628 | 12/1975 | Droegemueller et al. . |
| 4,085,743 | 4/1978 | Yoon ........................................ 606/140 |
| 4,211,231 | 7/1980 | Rzasa . |
| 4,376,376 | 3/1983 | Gregory . |
| 4,412,538 | 11/1983 | Yamauchi et al. . |
| 5,078,713 | 1/1992 | Varney . |
| 5,108,390 | 4/1992 | Potocky et al. . |
| 5,139,496 | 8/1992 | Hed . |
| 5,147,355 | 9/1992 | Friedman et al. . |
| 5,275,595 | 1/1994 | Dobak, III ................................ 606/23 |
| 5,281,215 | 1/1994 | Milder . |
| 5,400,602 | 3/1995 | Chang et al. . |
| 5,403,309 | 4/1995 | Coleman et al. . |
| 5,452,582 | 9/1995 | Longsworth . |
| 5,520,682 | 5/1996 | Baust et al. . |
| 5,554,172 | 9/1996 | Homer et al. . |
| 5,573,532 | 11/1996 | Chang et al. . |

OTHER PUBLICATIONS

Peter et al. Technique of Gastric Freezing in the Treatment of Doudenal Ulcer, *AMA*, Sep. 1, 1962, pp. 99–102.

Rufus, et al. A Co–Operative Double–Blind Evaluation of Gastric "Freezing" in the Treatment of Doudenal Ulcer, *The New England Journal of Medicine*, vol. 281, No. 1, Jul. 3, 1969, pp. 16–19.

*Primary Examiner*—Michael Powell Buiz
*Assistant Examiner*—Julian W. Woo
*Attorney, Agent, or Firm*—Cushman Darby & Cushman Intellectual Property Group of Pillsbury Madison & Sutro LLP

[57] ABSTRACT

A cryoprobe instrument for endoscopic use has been provided that permits the delivery of liquid or gaseous cryogens in the form of a spray. In an embodiment, the cryoprobe instrument includes an elongated, flexible tube having a fluid passage defined therethrough; a proximal connector portion provided at the proximal end of the tube for coupling the tube to a pressurized source of cryogenic refrigerant; and a nozzle tip mounted to the distal end of the tube. The nozzle tip has an outlet orifice constructed and arranged such that through the Joule-Thompson effect, cryogenic refrigerant exiting through the outlet orifice rapidly and substantially expands and cools.

20 Claims, 3 Drawing Sheets

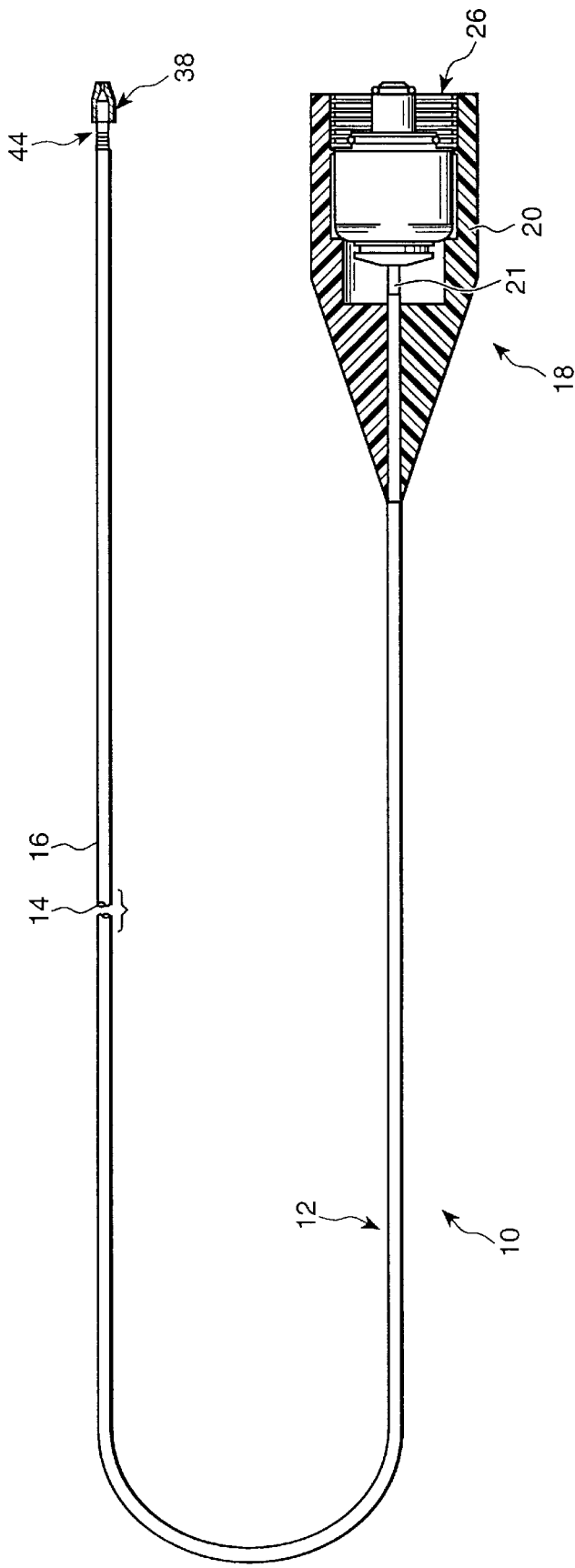

ENDOSCOPIC CRYOSPRAY DEVICE

BACKGROUND OF THE INVENTION

1. Field of the Invention

The present invention relates to a product and process for rapid hemostasis and/or tissue ablation in patients with gastrointestinal bleeding.

2. Description of the Related Art

Gastrointestinal (GI) bleeding is a major cause of morbidity and mortality throughout the world. The most common and important lesions are gastric and duodenal ulcers, esophageal and gastric varices, hemorrhagic gastritis, tumors and vascular malformations. The initial approach to diagnosis and attempted treatment of such lesions consists of endoscopy. The usual endoscopic modalities for the treatment of GI bleeding consist of thermal devices (e.g., bipolar cautery or laser for non-variceal bleeding vessels), injection therapy (e.g., sclerotherapy for varices and a variety of solutions for non-variceal bleeding vessels) or mechanical ligation (rubber-band ligation of esophageal varices). While such techniques have enjoyed considerable success in clinical practice, there remains several situations where their use has been associated with unsatisfactory results.

Since almost all the existing modalities above rely on some form of tissue contact, it is essential to be able to obtain a clear view of the actual bleeding lesions before they can be effectively employed. This is usually not possible with active variceal bleeding or arterial pumping, when the blood accumulates rapidly in the lumen and obscures the underlying mucosa. Endoscopic laser is the exception in that it does not require contact. However, the laser beam still has to be aimed accurately at the target lesion. Otherwise, indiscriminate damage to surrounding tissue will result with potentially serious consequences. Furthermore, laser systems are expensive and usually not transportable to the intensive care setting where the majority of these bleeders will be endoscoped.

Some lesions, such as gastric varices have not been treated very successfully with any of the modalities discussed above, whether they are actively bleeding or not. This is because of their peculiar anatomical features, for example, size of vessel, volume of blood flow, sub-mucosal location, etc. Thus, this remains a major threat to life in cirrhotics despite successful sclerotherapy of esophageal varices.

Another example of this is hemorrhagic gastropathy, particularly in patients with coagulation disorders such as those commonly seen in the oncology ward of medical facilities. The bleeding of the stomach occurs in a diffuse fashion from minute mucosal and sub-mucosal vessels and does not respond to any of the standard methods of treatment.

There are still other situations where the present modes of treatment, though effective, are associated with considerable problems. An example is bleeding from multiple vascular malformations in the colon, one of the most common causes of lower GI bleeding in the elderly. The treatment of choice is considered to be laser. However, in addition to the drawbacks listed above, such as their expense and non-portability, laser treatment may be tedious and time consuming as there may be literally hundreds of these lesions in the colon, each of which must be targeted individually. Further, after such extensive treatment, there is a risk of thermal injury to the colon.

Cryotherapy, or the use of extreme cold, is based on the principle that short applications of extreme cold can produce localized tissue destruction. Cryotherapy is used widely in dermatology, ENT, and gynecology for a variety of lesions ranging from tumors, hemangiomas, dysplasia, tonsillectomies, epistaxis and even hemorrhoids. Until very recently, so-called cryosurgery has been applied primarily to the outer surface of the body; however, recent advances in cryosurgery have enabled its application to the removal of unwanted tissue deep in the body. To that end, cryosurgical probes have been developed that use direct expansion of liquid refrigerant R12, carbon dioxide, nitrous oxide and other materials having two phase characteristics in the desired temperature range. The above-mentioned materials can produce temperatures, e.g., in the range from $-29°$ C. to $-88°$ C. for the purpose of killing tissue in surgical procedures. Liquid nitrogen ($LN_2$), which has a boiling point of $-196°$ C. at atmospheric pressure, has also been used as a cryogenic refrigerant in probes. Indeed, many conventional cryoprobe instruments operate with liquid nitrogen or other liquefied gas as the cooling medium.

In typical, conventional cryoprobes, the cryogenic refrigerant, for example $LN_2$, is introduced through a feed or delivery tube to an expansion chamber at the closed probe tip. As the cryogenic refrigerant enters the expansion chamber, it rapidly vaporizes and expands several hundred fold in volume. As the liquid vaporizes, it absorbs heat from the probe tip to lower its temperature, i.e. in the case of $LN_2$ to its normal boiling point (about $-196°$ C. at one atmosphere). Typically the diameter of the probe tip has been maintained as small as possible to afford accuracy and control to the user. Thus, some probes provide very small cold surfaces for surgical procedures in the eye, brain or heart, although other probes have required larger surfaces and more cooling power for operation on larger tissue volumes and areas.

Thus, in general, cryoprobes proposed for internal applications have been closed end cryoprobe instruments to afford control and precision. For dermatological and other applications on the outer surface of the body, on the other hand, several devices for spraying cryogens have been proposed and/or are available in the market.

SUMMARY OF THE INVENTION

We have recognized that there remains a need for an alternative means of endoscopic hemostasis and/or tissue ablation having the following particular characteristics:

1) An ability to be used from a distance in a relatively non-specific manner over a very large area, with adequate hemostasis at the bleeding site and minimal damage to surrounding tissue;
2) An ability to safely obliterate large vessels such as gastric varices;
3) Affordability; and
4) Technique simplicity.

It is thus an object of the invention to provide an alternative means of endoscopic hemostasis and/or tissue ablation characterized in that it fulfills most if not all of the criteria noted above.

We recognized that because the depth of injury can be precisely controlled, cryotherapy may be particularly suitable for the treatment of superficial dysplasic/neoplastic or vascular lesions. Moreover, we recognized that cryotherapy may address the problems associated with GI hemostasis noted above.

In examining the suitability and adaptability of cryotherapy to GI use, two issues of importance were examined. First, the effects of freezing on blood vessels were examined.

The other issue of importance considered was the effects of cryotherapy on GI tissue. In respect to both these issues, the suitability of cryotherapy was confirmed, as detailed below. Indeed, a major advantage of this proposed therapy was the excellent hemostasis achieved even in patients with impaired coagulation.

To address, in particular, the first and fourth criteria noted above, applicants proposed to spray the cryogen at the target bleeder.

Several spray devices for the use of cryogens are available in the market mainly for dermatological indications. In order to adapt such devices for endoscopic use, two unique considerations had to be addressed. It was recognized that it would be difficult, considering the length of the delivery system, to maintain the cryogen at low temperature. Indeed the length of any useful endoscopic accessory catheter (about 1.5 meters) would make it difficult to maintain the cryogen at low temperature before it exits from the terminal orifice. In addition, flexibility of the device was considered. To meet the foregoing criteria, applicants have proposed to furnish the refrigerant from a high pressure supply that may be maintained at room temperature through an elongated flexible line and to utilize the Joule-Thompson effect at the distal end of the line to provide a suitable extremely cold spray at the target site. Because many cryogenic refrigerants can, under suitable conditions, be conducted at or near ambient temperature, the line need not be substantially insulated, thus its flexibility can be maximized and its diameter minimized for disposition through an endoscopic device.

Thus, the foregoing and other objects of the invention are realized by utilizing cryotherapy to treat gastrointestinal bleeding. In accordance with a preferred embodiment of the invention, a cryoprobe instrument for endoscopic use has been provided that permits the delivery of liquid or gaseous cryogens in the form of a spray.

These and other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the

BRIEF DESCRIPTION OF THE DRAWINGS

FIG. 1 is a schematic elevational view of a cryoprobe instrument with a flexible tube portion and spray tip provided in accordance with the present invention;

DETAILED DESCRIPTION OF THE PRESENTLY PREFERRED EXEMPLARY EMBODIMENT

Figure 2A:
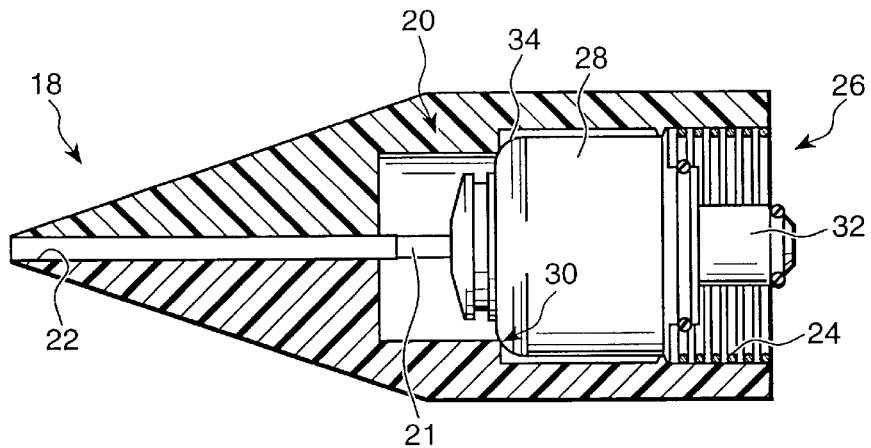
FIG. 2A is an enlarged schematic view, partly in cross-section, of a proximal connector portion provided in accordance with invention.

As noted above, in examining the suitability and adaptability of cryotherapy to GI use, two issues of importance were examined. First, the effects of freezing on blood vessels was examined. Most vessels less than 2 mm in size will exhibit an arrest of blood flow substantially immediately upon application of freezing temperatures. Large arteries appear resistant to the effects of cold injury and are able to preserve the wall structure intact despite freezing. This is important as it diminishes the risk of late rupture or aneurysm formation from inadvertent freezing of such vessels. Veins, particularly those small in size, appear to be more susceptible in that they may undergo thrombosis, (a desirable effect in variceal bleeding), though again with their wall structure intact. At the capillary level, thrombosis is more uniform, again a desired effect in hemorrhagic gastropathy and certain vascular malformations.

The other issue of importance considered was the effects of cryotherapy on GI tissue. In the late 1950s and early 1960s, gastric freezing to temperatures as low as −20° C. were used in hundreds of patients with peptic ulcers. For these investigations, a closed loop ethanol applicator was used. Specifically, a balloon was passed through the mouth to the stomach.

Although this therapy has since been abandoned, its use generated information on the effects of freezing temperatures on human stomachs. By and large, cold injury appears from those results to be well tolerated. From a review of 934 freezing procedures done in 696 patients it is seen that 26 developed a gastric ulcer, three with perforation and there were no deaths.

Several spray devices for the use of cryogens are available in the market, mainly for dermatological indications. In order to adapt such devices for endoscopic use, several unique considerations had to be addressed. For example, we recognized that it would be difficult, considering the length of the delivery system, to maintain the gas at low temperature. In addition, we recognized that flexibility was an essential feature because of the nature of endoscopy, requiring any accessory device to be able to bend along with the turns that the endoscope will undertake. To address these concerns, as noted above, we proposed to furnish the refrigerant from a high pressure cryogenic refrigerant supply that may be maintained at room temperature, to conduct the cryogenic refrigerant at or near ambient temperature to the target site, and to use the Joule-Thompson effect at the distal tip to achieve the freezing temperatures appropriate for rapid haemostasis and/or tissue ablation in accordance with the invention. As a consequence, we recognized that the elongated tube portion of the cryoprobe would have to be able to withstand the high pressures of the cryogenic refrigerant conducted therethrough. Due to modest variations in the tubing inner diameter resulting from manufacturing processes and other unavoidable pressure and hence temperature fluctuations along the tubing, as well as the potential for conducting cryogenic refrigerants such as liquid nitrogen which will be conducted below ambient temperature, we also recognized that the elongated tube portion of the cryoprobe would be subject to temperature fluctuations and potential temperature extremes and yet would have to retain a flexibility appropriate to endoscopic applications.

The invention was derived from a consideration of the criteria summarized above.

Thus, the cryospray device 10 (also referred to herein as a cryoprobe instrument) provided in accordance with the invention is adapted to be slidably inserted through an endoscope and to conduct cryogenic refrigerant from a high pressure supply to target tissue disposed beyond its distal end. To that end, and so as to be suitable for a variety of endoscopic applications, particularly in the gastrointestinal system, the cryoprobe instrument 10 provided in accordance with the present invention has a length of at least about 1 meter and more preferably on the order of at least about 1.5 m. While suitable lengths will depend on the scope with which the cryoprobe is to be used, it is not expected that a length of greater than about 3 meters will be necessary.

Furthermore, to withstand the pressure of the cryogenic refrigerant and to provide the requisite flexibility, in spite of temperature fluctuations, in accordance with a preferred embodiment of the invention, the elongated tube portion of the cryoprobe includes an elongated tube, preferably formed from stainless steel, such as fully annealed grade 304 stainless steel. In the presently proposed embodiment, the tube has a single cryogen delivery lumen. Moreover, to provide a lubricious surface, to facilitate feed through the bore of the endoscope; to provide a measure of insulation, to minimize loss of cooling effect; and to protect the stainless steel tube from excess bending or kinking, a thin polymeric layer or tube is provided in concentric relation to the stainless steel tube. A double-walled or polymer coated tube may be provided. In an exemplary and currently preferred embodiment, the thin outer layer or tube is provided by a thin walled polytetrafluoroethylene (TEFLON) tube 16 disposed in concentric relation to the stainless steel tube 14. Moreover, while TEFLON is presently preferred, other materials that may be suitable for the outer insulating/protective layer include polyethylene, polypropylene and the like.

In order that the cryoprobe may be fed through an endoscope to a target site, the outer diameter of the tube portion 12 must not be greater than the passage defined therefor through the endoscope. Thus, the outer diameter of the tube portion of the cryoprobe instrument should preferably be about 5 mm or less (0.197 inches) and more typically between about 2.25 and 3.30 mm (0.09–0.13 inches). Further, as presently proposed, a suitable tube portion would be one having an inner diameter of about 0.037 to about 0.039 inches (about 0.94 mm to about 0.99 mm) where the cryogen pressure is between a minimum of about 450 psi and a maximum of about 600–750 psi. An inner diameter in the recited range advantageously provides for a steady flow of cryogenic refrigerant from source to tip. If the inner diameter is too small, then depending upon the cryogen, the source pressure, and the like, the resulting flow restriction may result in undesirable cooling along the tube length. The upper limit depends upon the endoscope bore diameter and the combined thickness of the stainless steel and TEFLON tubes, as well as the desirability of avoiding undue cryogen expansion before the cryogen exits the nozzle. In an exemplary embodiment, the stainless steel tubing 14 has an outside diameter of 0.049 to 0.051 inches (1.25 to 1.30 mm) and a wall thickness of about 0.006 inches (0.152 mm). Further, in an exemplary embodiment, the TEFLON tube layer 16 has an outside diameter of about 0.09 to 0.125 inches (2.29–3.18 mm) and a wall thickness of about 0.010 inches (0.254 mm). By way of example, a cryoprobe instrument has been constructed in accordance with the invention, and has a tube portion having an inner diameter of about 0.037–0.039 inches (0.94–0.99 mm) and a polymer tube outer diameter of about 0.090 inches (2.29 mm).

As is apparent from the foregoing, the outer and inner diameters of the stainless steel tube and the polymer layer/tube provided will depend upon the flow passage diameter deemed appropriate, the wall thicknesses of the tubes, whether a gap between the tubes is necessary or desirable, the diameter of the endoscope bore, manufacturing tolerances of the respective parts and the like.

With reference to FIG. 2A, a proximal connector portion 18 is provided at the proximal end of the elongated flexible tube portion 12 for selectively interconnecting the same to a source of pressurized cryogen, e.g. a cryosurgical system. A suitable such system would desirably be one having a cryogenic refrigerant stored at a pressure of about 700 psi in a 9 oz. or larger storage vessel.

Figure 2B:
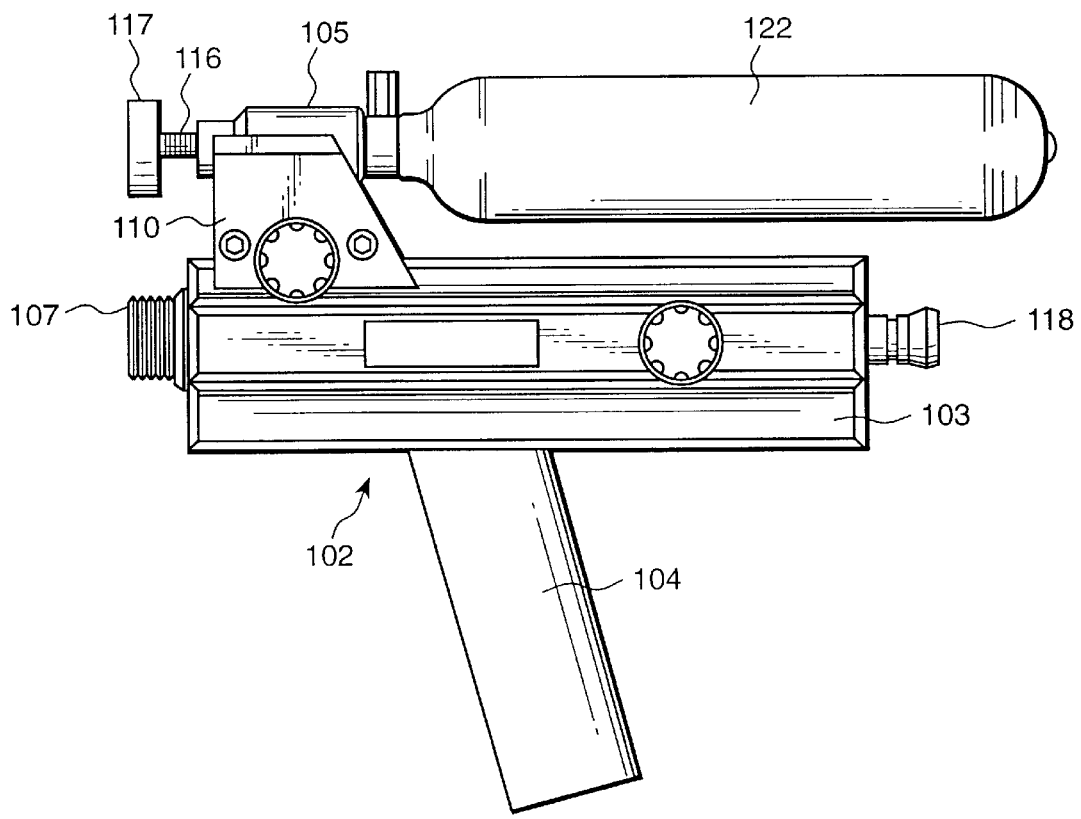
FIG. 2B is a schematic view of a cryogen system with which the cryoprobe of the invention may be used.

A portable hand held cryosurgical apparatus suitable for use with this invention is illustrated in FIG. 2B and comprises two elements, hand unit 102 and a pre-charged cylinder of cryogen 122. The arrangement of these elements is such that the balance of the apparatus renders it comfortable and easy to use.

Hand unit 102 comprises body 103 which is a substantially rectangular block of thermally insulative material with handle 104 extending downwardly from one side. Preferably body 103 and handle 104 are molded or milled from a light weight, thermally insulative plastic material such as polypropylene, polystyrene, polytetrafluoroethylene, fiber reinforced polymers, and the like. On the upper surface of body 103 is first coupling 105 which receives cylinder 122. Preferably first coupling 105 employs a mechanism which facilitates ease of changing from one cylinder to another during a cryosurgical procedure. Typically, since cylinders are produced with threaded necks, a threaded mechanism could be provided as first coupling 105. However, other quick disconnect mechanisms may also be used such as bayonet connectors, detent mechanisms employing a spring-loaded retaining collar such as are commonly used on hoses, and the like. A principal requirement for first coupling 105 is that it receive and hold cylinder 122 and that it provide a leak-free connection with cylinder 122. First coupling 105 is supported by support member 110 which is attached to body 103 and also supports cylinder 122 when it is in place.

First coupling 105 includes a means to puncture the seal of cylinder 122 to permit flow of cryogen from cylinder 122 via a conduit (not shown) in support member 110 into body 102 and, when the system is actuated, to the cryoprobe instrument 10. This puncturing means may be a simple screw 116 having a puncturing point which is driven into seal of cylinder 122 by turning knob 117.

In addition or in the alternative a coupling 118 may be provided at the axial end of body 102 to receive and hold a cylinder 122 in a manner similar to coupling 105.

At the forward end of body 103 is coupling 107 which removably receives cryoprobe 10 and provides a leak free seal therewith. Coupling 107 may be a threaded coupling or a quick disconnect coupling as described below which connects to the cryogen flow line within cryoprobe 10. Although a more sophisticated control system may be provided, for the purposes of endoscopic haemostasis and/or tissue ablation in the gastrointestinal tract, an "on-off" valve can be provided for enabling and disabling cryogen flow from the source to the cryoprobe. If deemed advantageous or desirable, temperature, pressure or other sensors may be provided to monitor the cryogen delivery to and/or through the cryoprobe.

By way of example, a suitable cryosurgical system, as briefly described above, with which the cryoprobe instrument of the invention may be used has been developed by Cryomedical Sciences Inc. of Rockville, Md., and embodiments thereof are disclosed in provisional application Ser. No. 60/034,876, filed Jan. 27, 1997, the entire disclosure of which is incorporated herein by this reference.

Returning to FIG. 2A, in the illustrated embodiment, the proximal connector portion is defined by a cover/connector subassembly designed to achieve a fluid tight coupling with a suitable pressurized cryogenic refrigerant source. More particularly, an e.g. plastic cover component 20 is provided in surrounding relation to a connector portion 26. The cover component 20 has a bore defined therethrough, including a distal bore portion 22 defined through the distal end thereof to slidably accommodate the flexible tube portion 12 of the cryoprobe 10 and to maintain the proximal segment thereof axially oriented with respect to the connector component 26. The proximal end of the cover has a coupling configuration 24 complementary to the coupling configuration provided on the cryogen source with which it is adapted to be used. In the illustrated embodiment, the cover component 20 has a female screw thread coupling 24 to receive the complementary male screw threads on the refrigerant outlet 107 of the cryosystem (FIG. 2B). However, other quick connect couplings such as bayonet, luer, or other such complementary engagement structures may be employed.

Figure 3:
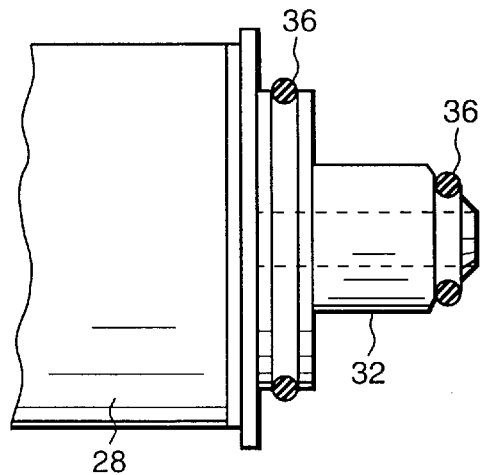
FIG. 3 is a broken away elevational view, partially in cross-section, of the connector component provided in accordance with the invention.

With reference to FIGS. 2A and 3, the connector component 26 provided within the cover component 20 is operatively coupled to the proximal end of the flexible tubing 12 of the cryoprobe 10 for being selectively operatively coupled to the refrigerant outlet of the cryosurgical system, upon coupling engagement of the cover 20 to the connector structure 107 of the cryosystem. More particularly, in the illustrated embodiment, the connector component 26 includes, for example, a stainless steel hub 28 mounted to the proximal end of the stainless steel tube 14. The connector component has a bore defined therethrough that is fluidly coupled to and/or disposed in surrounding relation to a portion or the entirety of the tube portion 12. In an exemplary embodiment, the inner stainless steel tube 14 of the tube portion 12 extends through the connector component 26 whereas the outer polymer tube 16 terminates at or adjacent the proximal end thereof. A nipple 21 may be provided to extend distally of hub 28, as schematically shown in FIGS. 1 and 2A, to receive the stainless steel tube 14 therewithin and the outer polymer tube 16 thereabout outer polymer tube 16.

The hub 28 of connector component 26 includes a shoulder or flange portion 30 for being abutted by the cover 20, and a male coupling 32 for selectively engaging the cryosurgical system outlet. Thus, as the cover 20 is engaged with the cryosurgical system and, e.g., rotated so as to be coupled thereto, a shoulder portion 34 within the cover component engages the flange portion 30 of connector component 26 so that the connector component 26 moves with it to the right, in the orientation of FIG. 2A, whereby male coupling 32 engages a correspondingly shaped outlet orifice of the cryosurgical system. Displacement of the male coupling into engagement with the refrigerant outlet in this manner operatively couples the flexible tube portion 12 of the cryoprobe with the source of cryogen, whereby selective actuation of the cryosystem to dispense pressurized refrigerant effects delivery of the refrigerant under pressure to and through the flexible tube portion 12 of the cryoprobe 10. A suitable sealing structure, such as O-rings 36, as illustrated, ensure that a fluid tight seal is achieved between the cryoprobe and the source of cryogenic refrigerant.

Figure 4A:
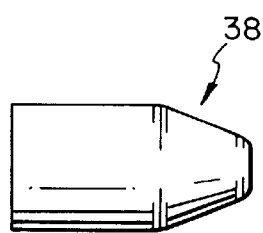
FIG. 4A is an elevational view of a distal spray tip nozzle provided in accordance with the invention.
Figure 4B:
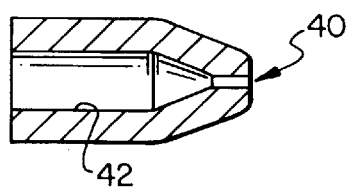
FIG. 4B is a schematic cross-sectional view of the nozzle.
Figure 4C:
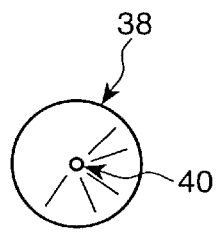
FIG. 4C is an end view of the nozzle, taken from the right in FIG. 4B.

A spray nozzle 38 is defined at the distal end of the cryoprobe 10. In accordance with the Joule-Thompson effect, the refrigerant expands as it exits the nozzle tip and becomes extremely cold. An exemplary nozzle tip is illustrated in FIGS. 4A–C. By way of example, a cryoprobe has been constructed in accordance with the invention, and has a nozzle tip outlet orifice 40 having a diameter of approximately 0.011–0.0135 inches (0.28–0.34 mm). On the other hand, the main conduit 42 of the nozzle has an inner diameter on the order of 0.058 inches (1.47 mm), and thus more closely approximates the outer diameter of the stainless steel tubing. Indeed, in an exemplary embodiment, the inner diameter of the nozzle is larger than the outer diameter of the stainless steel cryogen supply tube so that the distal end of tube 14 can be received therein and affixed thereto, e.g. by soldering or welding. Although not shown in the enlarged view of FIG. 4, a nipple 44 may be provided to extend proximally of nozzle 38, as schematically shown in FIG. 1, to receive the outer polymer tube 16.

Thus, discharge of the pressurized refrigerant from the cryosurgical system directs the liquid nitrogen or other cryogenic refrigerant under pressure along the flexible probe to the distal nozzle tip. Expulsion of the cryogenic refrigerant from the tip, taking advantage of the Joule-Thompson effect, results in rapid expansion thereof as a spray and rapid cooling thereof, thereby rapidly reducing the temperature of the target tissue. Visual observation of the target site through the endoscope can confirm achievement of hemostasis and/or sufficient cooling of the target tissue and/or whether additional application of cryogen is indicated.

Proper disposition of the cryoprobe tip 38 relative to the distal end of the endoscope and relative to the target tissue can be visually confirmed through the endoscope. Likewise, haemostasis and tissue ablation can be monitored during and a following spray application of the cryogen The feasibility of using this procedure for superficial tissue ablation and hemostasis in the gastrointestinal tract was tested as detailed in the following example.

EXAMPLE

Method

The cryospray device in accordance with the invention as described above was provided, through which liquid nitrogen ($-196°$ C.) was driven by a cryosurgical system. The elongated flexible tube portion was passed through the biopsy channel of a therapeutic upper endoscope that was positioned several centimeters away from the target lesion.

In the first set of experiments, liquid nitrogen was sprayed at the distal esophageal mucosa of five dogs. The dogs were then re-endoscoped periodically and biopsies taken from the treated areas. In other dogs, cryotherapy was used for hemostasis in a bleeding ulcer model.

Results

Freezing of the esophageal mucosa, with a sharp demarcation margin from untreated mucosa, was visible within seconds of spraying liquid nitrogen. This was followed by slow thawing over the next few minutes. All dogs survived the procedure and appeared to thrive. At 24 hours, the epithelium was completely sloughed off with preservation of the sub-mucosa and deeper layers. No significant hemorrhage was seen. By three weeks, the esophagus was completely re-epitheliolized in three of four animals.

In the hemostasis experiments, bleeding ceased immediately after cryospraying of the lesions but resumed upon thawing in most cases.

Conclusion

These experiments have demonstrated the feasibility of endoscopic cryotherapy with several exciting implications for gastroenterologists. Its ability to cause a controlled depth of entry that is avascular may make it particularly valuable for treating superficial lesions such as Barrett's and AVMs. Further, it may also serve as a useful adjunctive measure to the treatment of bleeding lesions (such as varices) by virtue of its ability to produce a rapid cessation of bleeding from a distance.

The device provided in accordance with the present invention may also find advantage as a palliative treatment of GI cancers. Although laser is considered the treatment of choice for such lesions, because of its expense it is not available to most community gastroenterologists. The present invention provides an inexpensive alternative for providing such treatment at facilities, especially where lasers are not readily available.

It will be realized that the foregoing preferred specific embodiments of the present invention have been shown and described for the purposes of illustrating the functional and structural principles of this invention and are subject to change without departure from such principles. Therefore, this invention includes all modifications encompassed within the spirit and scope of the following claims.

What is claimed is:

1. A cryoprobe instrument for conducting a cryogen through an endoscopic structure and spraying the cryogen towards a target site within a patient, comprising:

an elongated, flexible tube portion having a proximal end and a distal end, and a fluid passage defined therethrough;

a proximal connector portion provided at the proximal end of said tube portion for operatively coupling the tube portion to a pressurized source of cryogenic refrigerant;

a nozzle tip mounted to said distal end of said flexible tube portion, said nozzle tip having an outlet orifice constructed and arranged such that through the Joule-Thompson effect, cryogenic refrigerant exiting through said outlet orifice rapidly and substantially expands and cools, said outlet orifice having a diameter substantially less than a diameter of said fluid passage, said tube portion and nozzle tip mounted thereto being constructed and arranged for insertion through an endoscopic structure able to be disposed at least partly in the patient, said tube portion having a substantially constant diameter from said connector portion to said nozzle tip and said outlet orifice being in open communication with an exterior of the cryoprobe instrument, whereby cryogenic refrigerant exiting through said outlet orifice can be applied directly to the target site within the patient, a cryogenic refrigerant supply passageway being defined through the proximal connector portion and through the elongated flexible tube portion to said nozzle outlet of said nozzle portion for supplying cryogenic refrigerant to endoscopically accessed tissue disposed beyond said distal tip.

2. The cryoprobe instrument of claim 1, wherein the tube portion has a length of at least about 1 meter.

3. The cryoprobe instrument of claim 2, wherein the tube portion has a length of at least about 1.5 meter.

4. The cryoprobe instrument of claim 1, wherein the tube portion comprises a double walled, single lumen tube.

5. The cryoprobe instrument of claim 4, wherein said double wall structure comprises an inner wall defined by a stainless steel layer and an outer wall defined by a polymeric material.

6. the cryoprobe instrument of claim 5, wherein said polymeric material is polytetrafluorethylene.

7. The cryoprobe instrument of claim 1, wherein the flexible tube portion has an outer diameter of less than or equal to about 5 mm.

8. The cryoprobe instrument of claim 7, wherein the flexible tube portion has an outer diameter of about 2.8 mm.

9. The cryoprobe instrument of claim 1, wherein the outlet orifice of the nozzle tip has a diameter of about 0.28 to 0.34 mm.

10. A cryoprobe instrument for conducting a cryogen through an endoscopic structure and spraying the cryogen towards a target site within a patient, comprising:

an elongated, flexible tube portion having a proximal end and a distal end, and a fluid passage defined therethrough;

a proximal connector portion provided at the proximal end of said tube portion for operatively coupling the tube portion to a pressurized source of cryogenic refrigerant;

a nozzle tip mounted to said distal end of said flexible tube portion, said nozzle tip having an outlet orifice constructed and arranged such that through the Joule-Thompson effect, cryogenic refrigerant exiting through said outlet orifice rapidly and substantially expands and cools, said tube portion and nozzle tip mounted thereto being constructed and arranged for insertion through an endoscopic structure able to be disposed at least partly in the patient, said outlet orifice being in open communication with an exterior of the cryoprobe instrument, whereby cryogenic refrigerant exiting through said outlet orifice can be applied directly to the target site within the patient, a cryogenic refrigerant supply passageway being defined through the proximal connector portion and through the elongated flexible tube portion to said nozzle outlet of said nozzle portion for supplying cryogenic refrigerant to endoscopically accessed tissue disposed beyond said distal tip, wherein said proximal connector portion comprises a cover component and a connector component, said cover component having an engaging connector structure complementary to an engaging connector structure defined on a cryogenic refrigerant outlet of the pressurized source of cryogenic refrigerant for being detachably secured thereto, said connector component being configured to be fluidly coupled to the pressurized source of cryogenic refrigerant, said connector component including a hub portion provided adjacent the end of the tube portion, said cover component being generally coaxial with and being disposed in surrounding relation to at least a substantial portion of said hub portion.

11. A cryoprobe instrument for conducting a cryogenic refrigerant from a source of cryogen stored under pressure, through an endoscopic structure, and spraying the cryogen towards a target site within a patient, consisting essentially of:

an elongated, flexible tube portion having a proximal end and a distal end, and a single fluid passage defined therethrough;

a proximal connector portion provided at the proximal end of said tube portion for operatively coupling the tube portion to the source of cryogenic refrigerant; and a nozzle tip mounted to said distal end of said flexible tube portion, said nozzle tip having an outlet orifice constructed and arranged such that through the Joule-Thompson effect, cryogenic refrigerant exiting through said outlet orifice rapidly and substantially expands and cools, said tube portion and nozzle tip mounted thereto being constructed and arranged for insertion through an endoscopic structure able to be disposed at least partly in the patient, said outlet orifice being in open communication with an exterior of the cryoprobe instrument, said tube portion having a substantially constant diameter from said connector portion to said nozzle tip, whereby, a cryogenic refrigerant supply passageway is defined through the proximal connector portion and through the elongated flexible tube portion to said nozzle outlet of said nozzle portion for supplying cryogenic refrigerant to endoscopically accessed tissue disposed beyond said distal tip, whereby said tube portion can be disposed to extend through an endoscopic structure, and whereby cryogenic refrigerant exiting through said outlet orifice can be applied directly to the target site within the patient.

12. A method for producing sub-freezing temperatures sufficiently low to destroy living tissue by supplying a cryogenic liquid through an elongated tube disposed through an endoscope, comprising:

providing a cryoprobe instrument for conducting a cryogen through an endoscopic structure and spraying the cryogen towards a target site within a patient, including:

an elongated, flexible tube portion having a proximal end and a distal end;

a proximal connector portion provided at a proximal end of said tube portion for operatively coupling the tube portion to a pressurized source of cryogenic refrigerant;

a nozzle tip mounted to said distal end of said flexible tube portion, said nozzle tip having an out having an outlet orifice constructed and arranged such that through the Joule-Thompson effect, cryogenic refrigerant exiting through said outlet orifice rapidly and substantially expands and cools, said outlet orifice being in open communication with an exterior of the cryoprobe instrument;

providing a pressurized source of cryogenic refrigerant;

operatively coupling said cryoprobe instrument to said source of cryogenic refrigerant;

providing and disposing an endoscope so as to extend from a point outside a patient substantially to a target site within the patient;

feeding the cryoprobe instrument through the endoscope so that the nozzle tip thereof beyond a distal end of said endoscope and spaced from the target tissue;

conducting cryogenic refrigerant through the cryoprobe instrument so that the cryogenic refrigerant exits the distal, nozzle tip of the cryoprobe, expands, is substantially reduced in temperature, and is deposited substantially directly on tissue at said target site so as to substantially reduce the temperature thereof.

13. A process as in claim 12, further comprising the step of visually inspecting said target site through said endoscope after said step of conducting.

14. A process as in claim 13, further comprising repeating said conducting step after said visually inspecting step.

15. A process for immediate hemostasis in a patient with gastrointestinal bleeding comprising:

locating at least one source of gastrointestinal bleeding in the patient;

providing and disposing an endoscope structure so as to extend from a point outside the patient to a point adjacent said at least one source of gastrointestinal bleeding;

providing a cryoprobe instrument for conducting a cryogen through the endoscopic structure and spraying the cryogen towards adjacent said at least one source of gastrointestinal bleeding, said cryoprobe instrument including:

an elongated, flexible tube portion having a proximal end and a distal end;

a proximal connector portion provided at a proximal end of said tube portion for operatively coupling the tube portion to a pressurized source of cryogenic refrigerant; and a nozzle tip mounted to said distal end of said flexible tube portion, said nozzle tip having an outlet orifice constructed and arranged such that through the Joule-Thompson effect, cryogenic refrigerant exiting through said outlet orifice rapidly and substantially expands and cools;

providing a pressurized source of cryogenic refrigerant;

operatively coupling said cryoprobe instrument to said source of cryogenic refrigerant;

feeding the cryoprobe instrument through the endoscope structure so that the nozzle tip thereof is beyond a distal end of said endoscope structure but spaced from the at least one source of gastrointestinal bleeding;

conducting cryogenic refrigerant through the cryoprobe instrument so that the cryogenic refrigerant exits the distal, nozzle tip of the cryoprobe, expands, is substantially reduced in temperature, and is deposited on tissue at or adjacent said source of gastrointestinal bleeding so as to substantially reduce the temperature thereof, thereby to terminate said bleeding.

16. A process as in claim 15, further comprising the step of visually inspecting said source through said endoscope after said step of conducting.

17. A process as in claim 16, further comprising repeating said conducting step after said visually inspecting step.

18. A process for endoscopic, gastrointestinal tissue ablation comprising:

locating at least one target site for gastrointestinal tissue ablation;

providing and disposing an endoscope structure so as to extend from a point outside the patient to a point adjacent said at least one target site;

providing a cryoprobe instrument for conducting a cryogen through the endoscopic structure and spraying the cryogen towards adjacent said at least one target site, said cryoprobe instrument including:

an elongated, flexible tube portion having a proximal end and a distal end;

a proximal connector portion provided at a proximal end of said tube portion for operatively coupling the tube portion to a pressurized source of cryogenic refrigerant; and a nozzle tip mounted to said distal end of said flexible tube portion, said nozzle tip having an outlet orifice constructed and arranged such that through the Joule-Thompson effect, cryogenic refrigerant exiting through said outlet orifice rapidly and substantially expands and cools;

providing a pressurized source of cryogenic refrigerant;

operatively coupling said cryoprobe instrument to said source of cryogenic refrigerant;

feeding the cryoprobe instrument through the endoscope structure so that the nozzle tip thereof is beyond a distal end of said endoscope structure but spaced from the at least one target site;

conducting cryogenic refrigerant through the cryoprobe so that the cryogenic refrigerant exits the distal, nozzle tip of the cryoprobe, expands, is substantially reduced in temperature, and is deposited on tissue at said at least one target site so as to substantially reduce the temperature thereof, thereby to ablate at least a portion of said tissue.

19. A process as in claim 18, further comprising the step of visually inspecting said target site through said endoscope after said step of conducting.

20. A process as in claim 19, further comprising repeating said conducting step after said visually inspecting step.

* * * * *